(12) United States Patent
DiLeo

(10) Patent No.: US 7,104,422 B2
(45) Date of Patent: Sep. 12, 2006

(54) FLUID DISPENSING APPARATUS HAVING MEANS FOR MEASURING FLUID VOLUME CONTINUOUSLY

(75) Inventor: Anthony DiLeo, Westford, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/784,330

(22) Filed: Feb. 23, 2004

(65) Prior Publication Data

US 2004/0164092 A1    Aug. 26, 2004

Related U.S. Application Data

(60) Provisional application No. 60/449,621, filed on Feb. 24, 2003.

(51) Int. Cl.
*B67D 5/08*    (2006.01)

(52) U.S. Cl. .................. 222/64; 222/642; 222/204

(58) Field of Classification Search ............. 222/64, 222/639, 641, 642, 204; 137/139, 563, 396; 73/149, 861, 861.08, 861.12
See application file for complete search history.

(56) References Cited

U.S. PATENT DOCUMENTS

| | | | | |
|---|---|---|---|---|
| 4,262,542 A * | 4/1981 | Freund et al. ............ 73/861.12 |
| 4,401,141 A | 8/1983 | Rosen et al. ................ 141/192 |
| 4,806,847 A | 2/1989 | Atherton et al. ............... 324/61 |
| 4,888,989 A | 12/1989 | Homer ......................... 73/304 |
| 4,982,606 A | 1/1991 | Adamski et al. .............. 73/304 |
| 5,017,909 A | 5/1991 | Goekler ....................... 340/620 |
| 5,090,594 A | 2/1992 | Randall, Jr. et al. ............. 222/1 |
| 5,105,859 A | 4/1992 | Bennett et al. .............. 141/102 |
| 5,135,485 A | 8/1992 | Cohen et al. ................... 604/67 |
| 5,203,367 A | 4/1993 | Akai et al. ............. 136/101.25 |
| 5,480,063 A | 1/1996 | Keyes et al. .................. 222/64 |
| 5,680,960 A | 10/1997 | Keyes et al. .................. 222/64 |
| 5,806,716 A | 9/1998 | Vogt ............................. 222/59 |
| 5,896,900 A | 4/1999 | Haring et al. ............... 141/196 |
| 6,024,251 A | 2/2000 | Mayer et al. .................. 222/64 |
| 6,178,818 B1 | 1/2001 | Plochinger ................... 73/304 |
| 6,299,020 B1 * | 10/2001 | Sudolcan et al. ............... 222/1 |

OTHER PUBLICATIONS

"Acerta Disposable Filling System", Millipore Product Brochure, Lit No. PF 1200EN00 (Dec. 2002).
"NBK Bypass Level Gage, Switch, Transmitter", http://www.clarksol.com/html/prodspecsNBK.htm. (hardcopy dated Oct. 28, 2002).

* cited by examiner

*Primary Examiner*—Joseph A. Kaufman
(74) *Attorney, Agent, or Firm*—Millipore Corporation

(57) ABSTRACT

A fluid dispensing apparatus is described, the operation of which involves installation thereinto of a single-use fluid dispenser cartridge. The cartridge itself comprises a pliable fluid reservoir and a fill tube assembly. The fill tube assembly—the component which most immediately acquires and delivers a definable volume of fluid into a vial or other container—is characterized by its incorporation of means for continuously measuring fluid volume therein, particularly, as a function of electrical capacitance. Accuracy, precision, and reliability are improved. The apparatus can be used to dispense a broad range of fluids, including viscous fluids. No moving mechanical parts are required in the measurement of capacitance.

10 Claims, 5 Drawing Sheets

FLUID DISPENSING APPARATUS HAVING MEANS FOR MEASURING FLUID VOLUME CONTINUOUSLY

REFERENCE TO RELATED APPLICATION

This application claims the benefit of Provisional U.S. Patent Application Ser. No. 60/449,621, filed Feb. 24, 2003.

FIELD

In general, the present invention relates to fluid dispensing apparatuses, and more particularly, to a fluid dispensing apparatus having means for measuring continuously the volume of the fluid to be dispensed thereby.

BACKGROUND

Numerous types of fluid dispensing apparatuses exist.

For example, one type of fluid dispensing apparatus currently in widespread use is a positive displacement filler, which for fluid dispensation relies directly upon mechanical means that physically contact and positively displace fluid. Positive displacement fillers often use a piston and cylinder arrangement, wherein the backward movement of the piston draws fluid into a cylinder through an inlet and the forward movement of the piston expels the fluid through an outlet. Alternatively, a rotary pump can be used to displace fluid. Positive displacement pumps can operate at relatively high speeds, filling as many as six hundred bottles per minute, and can achieve levels of accuracy up to about ±0.5%.

A disadvantage of positive displacement fillers is that fluid, during operation, comes into contact with moving parts. As the moving parts wear, particulate matter can enter the fluid causing particulate contamination. If severe enough, particulate contamination can render the dispensed fluid product unusable.

Another disadvantage with positive displacement fillers involves the difficulty in cleaning and sterilizing its wet moving parts. In positive displacement pumps, the critical tolerances between pads, such as the piston and cylinder, precludes effective in situ cleaning. Thus, the user must disassemble the apparatus for cleaning and sterilization. This process is not only time consuming, but may result in biological contamination of the pads when handled by the mechanic during reassembly.

Another type of fluid dispensing apparatus is the time/pressure filler, which in operation generally relies upon a fluid reservoir maintained under relatively constant pressure. The fluid is dispensed from the reservoir through a compressible line. Fluid flow is shut off by a pinch type valve which squeezes and collapses the discharge line. A predetermined volume of fluid is dispensed by opening the discharge line for a pre-determined period of time and then closing the line. If the pressure within the fluid reservoir is maintained constant, an equal amount of fluid should be dispensed each time the cycle is repeated. However, it has been observed that time/pressure fillers often do not work as well in practice as they do in theory.

Another type of fluid dispensing apparatus is a volumetric fluid dispensing apparatus. A volumetric dispensing apparatus—such as shown in U.S. Pat. No. 5,090,594—measures a predetermined volume of fluid in a measuring cup or fill tube, then subsequently dispenses it into a receptacle. Volumetric fillers, although slower than positive displacement fillers, are accurate and avoid the problems of microbial and particulate contamination. However, volumetric fillers, like time/pressure fillers, depend on a relatively constant pressure. Pressure irregularities, such as may be occasioned upon use of clarification filters, can lead to inaccurate filing.

Another type of fluid dispensing apparatus is described in U.S. Pat. No. 5,480,063, issued to Keyes et al. on Jan. 2, 1996. Keyes et al. describe an apparatus having no moving parts in contact with the fluid being dispensed. The apparatus includes a fluid reservoir and a fill tube communicatively connected thereto. The fill tube forms a closed circuit with the fluid reservoir. In operation, fluid is transferred from the reservoir into the fill tube. When the fluid level in the fill tube reaches a predetermined height, fluid transfer is terminated, and fluid dispensed from the fill tube into a container.

The fluid dispensing apparatus of Keyes et al. provides advantages not found in the other types of fluid dispensing apparatuses, and accordingly, has become of late an area of considerable technical and commercial interest. Regardless, current embodiments—though they provide good results—can be improved. In particular, the current means used to monitor fluid levels therein—i.e., optical sensors—are effected by the optical properties of the fluid and on the mechanical assemblages that move the sensors correspondent with the rise and fall of fluid meniscuses. The level of a viscous fluid, which tend to coat interior wall surfaces, can be difficult to determine with precision. Further, the use of said mechanical assemblages (including, for example, a stepper motor) can generate particles at levels unacceptable for certain sterile applications.

SUMMARY

The present invention provides a fluid dispensing apparatus, the operation of which involves installation thereinto of a single-use disposable fluid dispenser cartridge provided with means for the electronic measurement of the volume of a fluid therein. Aside from said means, the cartridge comprises a pliable fluid reservoir and a fill tube assembly.

The pliable fluid reservoir, in a preferred configuration, expands and contracts passively to regulate (i.e., maintain constant) the internal pressure in said fluid reservoir. The pliable fluid reservoir is provided with a fluid inlet (for introducing fluid into the pliable fluid reservoir) and a fluid outlet (for the release of fluid from said pliable fluid reservoir). Preferably, the fluid reservoir is also provided with an upper opening to, for example, enable loop formation with said fill tube assembly.

The fill tube assembly—the component most immediately responsible for acquiring and delivering a definable volume of fluid into a vial or other container—is characterized by its incorporation of enabling means for continuously and electronically measuring fluid volume therein, particularly as a function of electrical capacitance.

In respect of its general structure, the fill tube assembly is connected to said pliable fluid reservoir's fluid opening, at one end, and to the fluid outlet, at another end, thereby forming a loop (i.e., a circular flow path) with said fluid reservoir. The fill tube assembly includes a first area suitable for provision of a fill valve in said loop (i.e., for controlling the flow of fluid released from said pliable fluid reservoir into the fill tube assembly). Also included is a drain line with a second area suitable for provision of a discharge valve (i.e., for dispensing a predetermined volume of fluid from said fill tube assembly).

In respect of its volume measuring functionality, the fill tube assembly is provided with at least two electroconductive terminals capable of being directly or indirectly connected to an energy source so that a current can be passed from one terminal to the other. The capacitance of said current can be assessed by the apparatus to determine the amount of fluid in the fill tube assembly. Based on such assessment, the fill valve and discharge valves are activated to either introduce more fluid into the fill tube assembly or dispense fluid therefrom into a suitable container.

Because no moving parts are in contact with the fluid, the fluid dispensing apparatus of the present invention reduces the risk of particulate contamination of the fluid. Additionally, the fluid dispenser cartridge can be removed and replaced between production runs, thereby reducing the costs associated with cleaning and sterilization.

Based on the foregoing, it is a primary object of the present invention to provide a fluid dispensing apparatus having means for continuously measuring the volume of liquid therein.

It is another object of the present invention to provide a fluid dispensing apparatus capable of measuring the volume of fluid to be dispensed thereby, wherein said fluid is comparatively viscous, and wherein said measurement is reasonably accurate and reliable.

It is another object of the present invention to provide a fluid dispensing apparatus capable of measuring the volume of fluid to be dispensed thereby, wherein said measurement does not require utilization of mechanical assemblages that can shed particles and other potential contaminants.

It is another object of the present invention to provide a fluid dispensing apparatus that can be calibrated relatively easily.

It is another object of the present invention to provide a single-use fluid reservoir with an integrated fill tube assembly (i.e., a single-use fluid dispenser cartridge), the fill tube assembly having means for enabling continuous measurement of the fluid volume therein, particularly as a function of electrical capacitance.

It is another object of the present invention to provide a single-use fluid reservoir with integrated fill tube assembly, having at least two electroconductive terminals connectable to an energy source so that a current can be passed from one terminal to the other.

With these and other objects in view, which will readily appear as the nature of the invention is better understood, the invention subsists in its novel combination of parts hereinafter more fully described and claimed.

DETAILED DESCRIPTION

Figure 1:
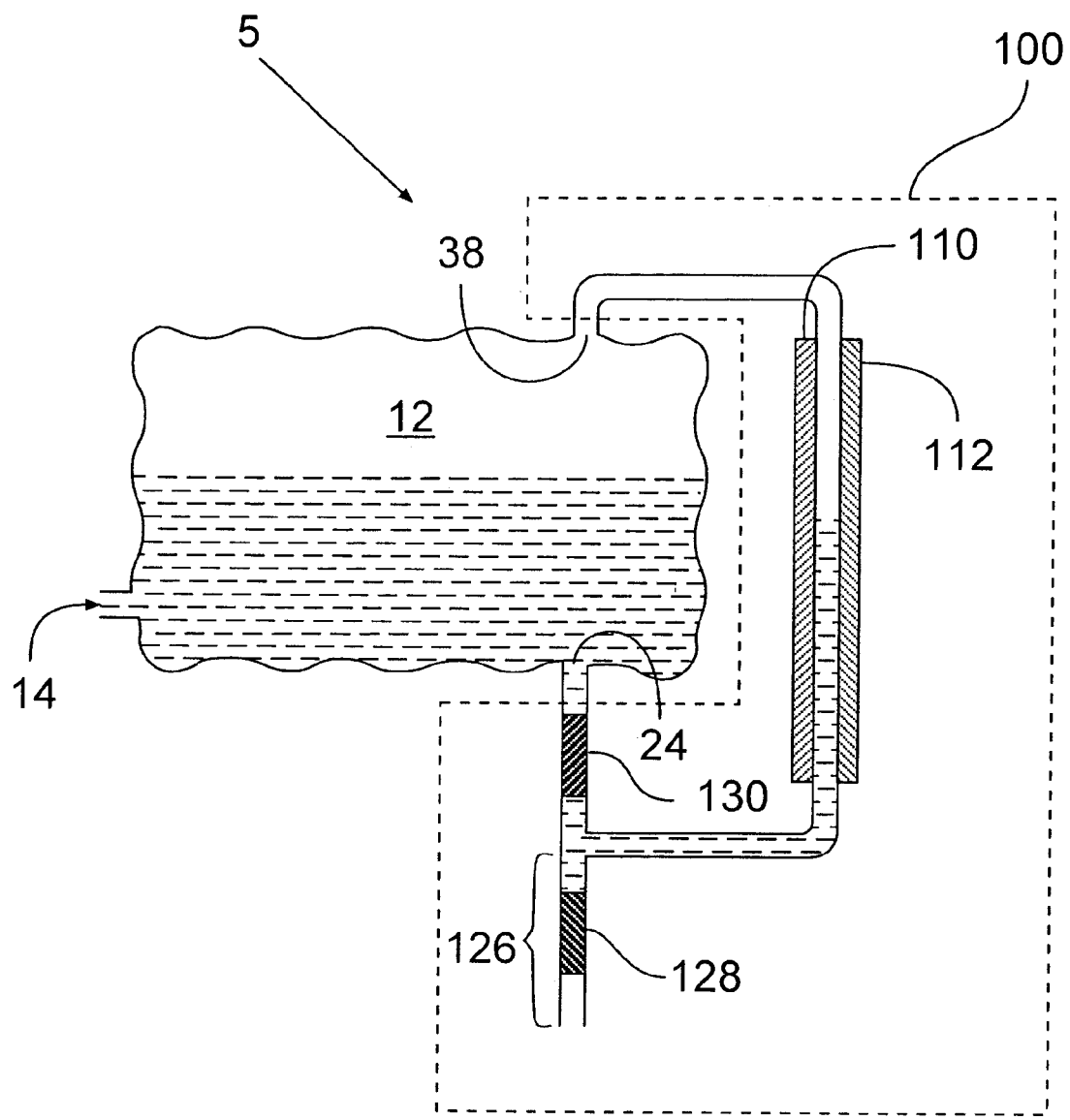
FIG. 1 is a schematic illustration of a single-use fluid dispenser cartridge 5 according to an embodiment of the present invention, the cartridge 5 capable of being installed into a fluid dispensing apparatus 10.

The present invention provides a fluid dispensing apparatus well suited, for example, for dispensing precisely and consistently into a container (or containers) measured volumes (or individual dosages) of pharmaceutical fluids, particularly viscous pharmaceutical fluids. The inventive apparatus is characterized by its accuracy (i.e., the apparatus can attain accuracy comparable to positive displacement pump systems); ease of operation (e.g., the apparatus does not require mechanical calibration); suitability for use in a pharmaceutical clean room (i.e., the apparatus has a reduced number of particle-shedding moving parts); and low maintenance (cf., uses a single-use fluid dispensing cartridge).

In general, the fluid dispensing apparatus comprises a hardware component into which is installed a disposable component that enables the collection, dispensation, and precise electronic measurement of fluid therein.

The hardware component comprises essentially all the "fixed" mechanical and electronic means (e.g., plumbing, circuitry, wiring, energy source, pumps, support structures, manifolds, valves, supply or other supplemental fluid reservoir, logic chips, and like sub-components) that enable a fluid to be brought into the disposable component and dispensed therefrom. The hardware component can vary considerably in its overall configuration and in its collection of sub-components in the different embodiments of the present invention, but its basic functionality of "operating" upon the disposable component remain the same throughout. Typically, the mechanical and electronic means forming collectively the hardware component will be contained in generally fixed arrangement within a rigid outer housing or cabinet.

The disposable component (i.e., the "fluid dispensing cartridge")—the key component of the present invention—is essentially a pliable fluid reservoir having an integrated fill tube assembly. It is "single-use" in the sense that at the completion of a fluid dispensing operation, the component can be either disposed (i.e., as is sometime required by law after dispensing certain environmentally-regulated substances) or recycled (e.g., after dispensing non-regulated substances). The single-use fluid dispensing cartridge is characterized by its incorporation of level sensing means by which the fluid level therein—a key measure that corresponds ultimately to the volume of fluid dispensed into a vial or other collection receptacle—can be determined continuously as a function of electrical capacitance or other electronic profile.

Certain enabling parts of the level-sensing means are incorporated as fixed, integral parts of the fluid dispensing cartridge. It is envisaged, however, that, the level-sensing means, in its entirety, can also be part of the hardware component, i.e., one that is brought into contact with the cartridge only during or immediately prior to a fluid dispensing operation.

In respect of one of its embodiments, the single-use fluid dispenser cartridge 5 comprises: (a) a pliable fluid reservoir 12 capable of expanding and contracting to regulate the internal pressure in said fluid reservoir, said pliable fluid reservoir having an upper opening 38, a fluid inlet 14 for introducing fluid into the pliable fluid reservoir 12, and a fluid outlet 24 for the release of fluid from said pliable fluid reservoir 12; (b) a fill tube assembly 100 connected to said upper opening 38, at one end, and said fluid outlet 24, at another end, forming a loop with said fluid reservoir 12, the fill tube assembly 100 comprising (i) a first area 130 suitable for provision of a fill valve in said loop for controlling the flow of fluid released from said pliable fluid reservoir 12 into the fill tube assembly 100, and (ii) a drain line 126 with a second area 128 suitable for provision of a discharge valve for dispensing a predetermined volume of fluid from said fill tube assembly 100; and (c) at least two electroconductive terminals 110 and 112 connectable to an energy source so that a current can be passed from one terminal to the other.

The operation of the fluid dispensing apparatus, in general terms, commences with the loading of the fluid reservoir 12 with the fluid for dispensation. This is accomplished by "opening" or otherwise rendering accessible the fluid inlet 14 into the fluid reservoir 12. At this point, a fill valve 30 at the fluid output end 24 of the fluid reservoir 12 is "closed". After loading the reservoir, the means by which fluid is introduced into the reservoir is "closed".

The next step involves loading the fill tube assembly 100 with fluid from the reservoir 12. This is accomplished by opening the fill valve 30, while keeping a drain valve 28 "closed". As the fluid gradually fills the fill tube assembly 100, its level therein is continuously monitored by the capacitance sensors, the data thereof being processed by an electronic control system. Once a certain capacitance is reached, suitable electronic signals (or prompts) are transmitted (or triggered) to effect immediately (or ultimately) the "closing" of fill valve 24.

Fluid is then dispensed from the fill tube assembly 100 into a vial or other container. This is accomplished by "opening" the drain valve 12 provided in the discharge tube, emptying substantially the fluid content of the fill tube assembly. Because the internal dimensions of the fill tube assembly, the capacitance properties of the fluid and its viscosity, and/or other like properties are known before hand, the amount of fluid that drains outs of the fill tube assembly can be predetermined within a reasonable degree of accuracy.

The present invention does not require all fluid to drain out of the fill tube assembly. The fill tube assembly can be configured specifically to retain some predetermined volume of fluid. Since the fluid retention volume is known beforehand, it can be factored into the control mechanisms, and thus, not compromise accuracy.

The "pliability" of the pliable fluid reservoir 12 can vary among different applications, influenced by such things as the expected external pressure, the rheological properties of the dispensed fluid, the configuration and internal volume of the fill tube assembly, and the like. The chemical properties of the fluid will likely influence the type of materials that can be used to make the pliable fluid reservoir, for example, certain fluids may require the use of less pliable, durable materials.

Although not a limit to the present invention, in respect of the dispensing of pharmaceutical fluids, the typical total internal volume of a fluid reservoir is presently expected to be in the range of about 1.5 liters to about 10 liters. With such volumes, the dimensions of the supply inlet, upper opening, and fluid output are as follows: The diameter of the supply inlet can range from about 0.25 inch to about 0.75 inch (about 0.635 cm to about 1.90 cm); the diameter of the upper opening can range from about 0.125 inch to about 0.75 inch (about 0.3175 cm to about 1.90 cm); and the diameter of the fluid outlet can range from about 0.125 inch to about 0.75 inch (about 0.3175 cm to about 0.1.90 cm). For greater volumes—particularly, if involving viscous fluids—these dimensions will be substantially larger.

Since the fluid dispenser cartridge is likely to be discarded, advantage is gained by assuring that the materials in this consumable component are off modest value. In this regard, it will be understood that comparatively costly sub-components—such as valves and complex and/or sophisticated electronic components—will likely not be part of the consumable, but rather permanent fixtures of the hardware component.

With regard to the aforementioned drain valve and fill valves, these will likely, but not necessarily, be of the pinch-type variety, mounted or otherwise disposed within the hardware component of the fluid dispensing apparatus. When a fluid dispenser cartridge is installed, specific regions of its fill tube assembly will be united with this valve (e.g., clipped into) such that their functionality can be realized. Pinch valves—in this light—can be seen as advantageous in that they don't require any cutting of tubes and mating of valve elements—a task generally requiring higher measure of technical proficiency. Rather, the specific regions of the tube only be sufficiently "pinchable", to permit the pinch valves to clamp down on the region sufficiently to collapse and shut the lumen of the tube. In this manner, the valves need not necessarily be part of the disposable element. Other means and approaches for rendering certain predesignated areas of the fill tube assembly suitable for engagement (or otherwise provision) therewith of flow controlling valves and the like are known and can be implemented.

The electronic circuitry enabling the capacitance detection should also be configured with an eye towards economy. Thus, for example, the consumable fluid dispenser cartridge includes the terminals, and perhaps some leads and wires, that can be plugged into and/or otherwise connected to appropriate dedicated sockets into the controller mechanism, which is part of the non-disposable hardware assembly.

The electronic terminals preferably comprise a pair of narrow metal strips, typically copper, that can be mounted or affixed permanently to desired regions of the fluid dispensing cartridge. In a typical configuration, the strips are mounted opposed to one another on the outside of the tube 40, traversing the entire working length of the "sighting region" of the fill tube assembly. Capacitance detection is accomplished by continuously passing a pulsed current across the space between the two metal strips. Since there is a significant difference between the capacitance of an empty air-filled tube and one that is liquid filled, the liquid volume can be continually monitored as it move up and down the tubing. The use of a "pulsed" current improves sensitivity and continuity of measurement over time, as well as accommodate—where relevant—the relatively low electrical capacity and quick discharge of copper electrodes. In certain instances, the temperature will also have to be measured, as it may have an effect on capacitance.

Alternatives exist to the placement of the copper strips on the outside surface of the fill tube assembly. For example, the copper strips can be mounted as follows: One is mounted on the outside of the tube (for example, towards a bottom portion thereof) and the second is placed inside the fill tube assembly suspended without touching the walls. This version is particularly appropriate for high viscosity fluids that tend to "cling" vigorously to the tube's side walls. To prevent unwanted chemical interaction between the internally mounted terminal and fluid loaded into the fill tube assembly, the internally mounted terminal is preferably coated with a chemically non-reactive polymeric material or otherwise protected or isolated with some other suitable barrier.

The sensitivity of measurement can be controlled by varying the relative widths of the metal strips, when and if used as terminals. For example, a desirable degree of sensitivity (with respect to certain applications) can be obtained by using a pair of strips of unequal widths, i.e., one wider than the other.

Aside from the fill tube assembly, it may also be advantageous for fluid level of the fluid reservoir to be monitored using capacitance sensors. This can be done independently of the use of capacitance sensors on the fill tube assembly, or—more preferably—in combination therewith.

The electroconductive terminal by themselves are not sufficient to render operable the fluid dispensing apparatus. The electroconductive terminals need to be wired or linked or otherwise connected to both an energy source and an electronic control mechanism, both of which can be integrated within single sub-component. The energy source essentially drives a current through both terminals, whilst the electronic control mechanism—for example, by incorporation therein of a potentiometer or like electronic sensor—measures the capacitance of said current and, based thereon, regulates the flow of fluid, for example, by selectively opening and/or closing the fill valve and/or the discharge valve.

The embodiments of the present invention illustrated in the Figures all involve use of a single fill tube assembly per reservoir. In practice, however, it may be more advantageous to use several fill tubes assemblies per reservoir. The basic configuration and function of such additional fill tube assemblies will essentially be the same as that described above.

In the operation of the fluid dispensing apparatus, the capacitance in the fill tube assembly is measured continuously, so that the volume of in the tube will be continuously determined, rather than determining certain minimum and maximum volumes. Since the capacitance sensor measures for liquid continuously, so-called "proportional-integral-derivative" (PID) controls for the system, rather than proportional controls, can be used to improve the dispense accuracy and repeatability.

Calibration of the capacitance system is simpler than the optical system because no trial and error is needed. Assuming that the inner bore or the fill tube assembly is nearly constant, a linear relationship between liquid height thus sensor output and volume dispense applies. Thus calibration need only measure three points on the relationship and the control logic device will be able to operate in accordance with the algorithm.

The present invention is capable of embodiment in varying configurations. For illustrative purposes, a few of such embodiments are illustrated in the Figures.

Figure 2:
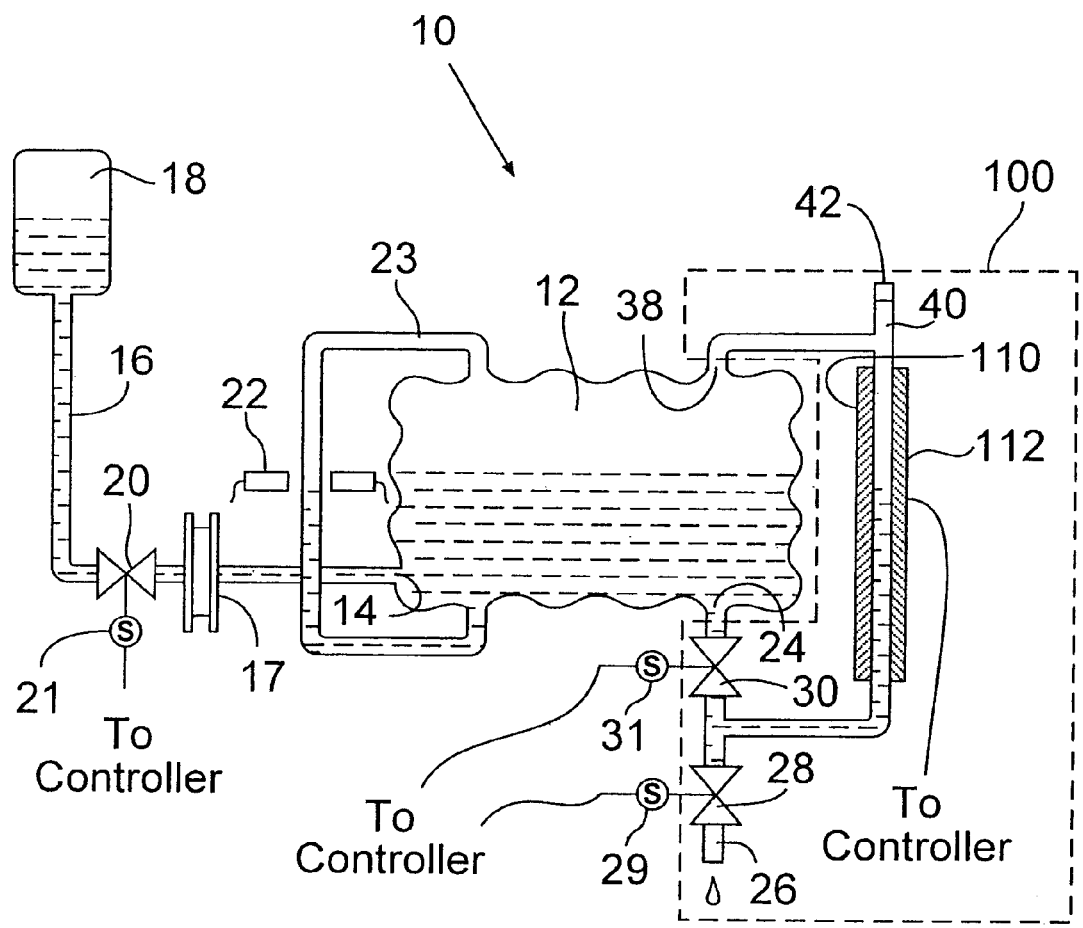
FIG. 2 is a schematic diagram illustrating an embodiment of the fluid dispensing apparatus 10 according to the present invention.

Attention is directed first to FIG. 2. A fluid dispensing apparatus according to a basic embodiment is shown therein indicated generally by the numeral 10. The fluid dispensing apparatus 10 includes a pliable fluid reservoir 12 having a fill port 14 (i.e., a fluid inlet) connected by a fluid supply line 16 to a fluid source 18. A sterilization or clarification filter 17 is disposed in the fluid supply line 16. The fluid reservoir 12 is a flexible bag-like enclosure which expands and contracts during operation. The fluid supply line 16 includes a supply valve 20 activatable by solenoid 21.

To maintain the fluid level in the pliable fluid reservoir 12 at a predetermined level, an optical fluid level sensor 22 is positioned along a measuring tube 23. (The optical fluid level sensor 22 and measuring tube can be replaced, if desired, by electroconductive capacitance-based sensors.) One end of the measuring tube 23 is connected to a lower portion of the pliable fluid reservoir 12, while the opposite end is connected to an upper portion of the pliable fluid reservoir 12. In operation, the level of fluid in the measuring tube 23 will rise or fall to match the level of fluid in the pliable fluid reservoir 12. The fluid level sensor 22 snaps around the outside of the measuring tube 23 and its vertical position determines the fluid level in the pliable fluid reservoir.

A programmable controller (not shown) is operatively connected to the fluid level sensor 22 and solenoid 21. When the fluid level in the pliable fluid reservoir 12 drops below the level of the sensor 22, the programmable controller opens supply valve 20 to introduce more fluid into the pliable fluid reservoir 12. Thus, the level of fluid in the pliable fluid reservoir 12 can be made constant or otherwise regulated. If desired, multiple sensors 22 can be used to define upper and lower limits.

The fluid reservoir 12 includes a drain port 24 (i.e., a fluid outlet) connected to a lower end of fill tube assembly 100. Another end of fill tube assemble 100 is connected to an upper opening 38 in the upper portion of the pliable fluid reservoir 12. Thus, the fill tube assembly 100 forms a loop with the pliable fluid reservoir 12. A fill valve 30 is disposed in the loop for controlling the flow of fluid from the fill reservoir 12 to the fill tube assembly 100. The fill valve 30 is controlled by solenoid 31 connected to the programmable controller.

A drain line 26 provided in the fill tube assembly 100 for dispensing fluid from the fill tube assembly 100 into a container. Drain line 26 includes a drain valve 28 for controlling said dispensing of fluid. The drain valve 28 is controlled by a solenoid 29 activatable by the programmable controller.

Figure 3:
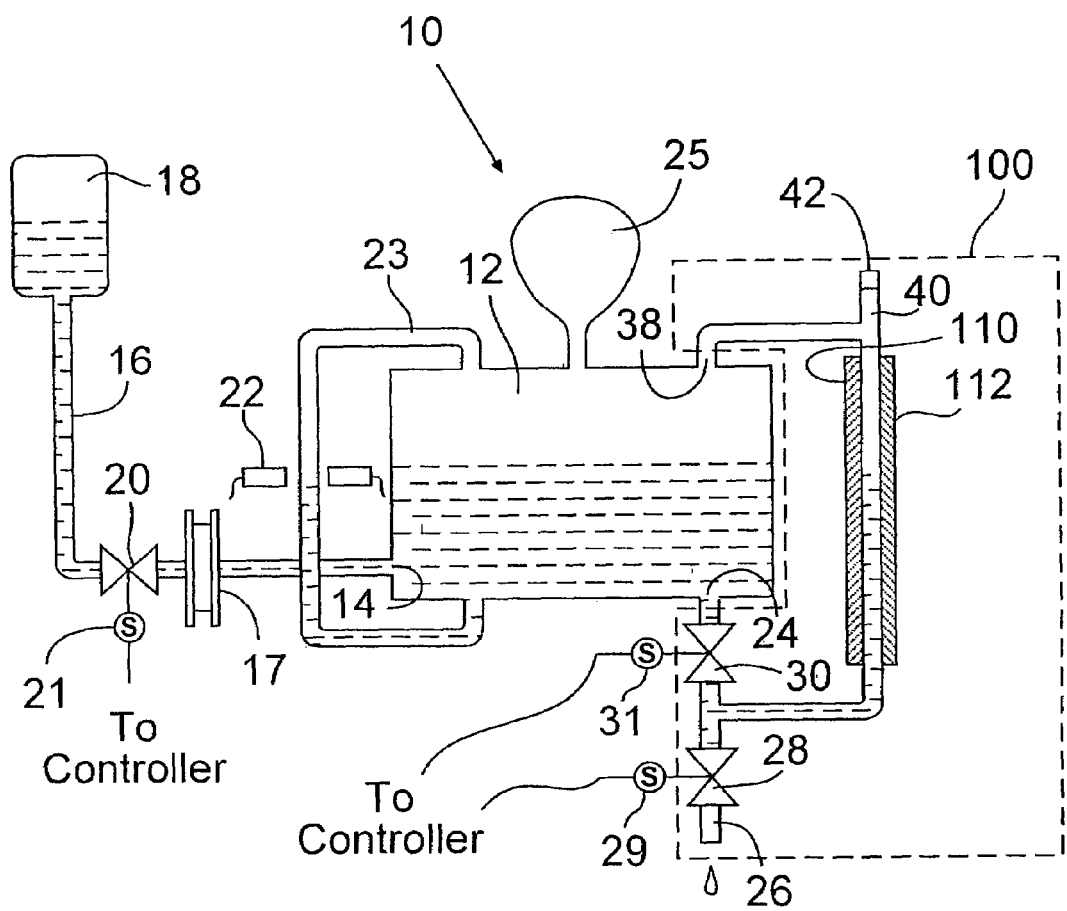
FIG. 3 is a schematic diagram illustrating another embodiment of the fluid dispensing apparatus 10 according to the present invention.

Another embodiment of the present invention is shown in FIG. 3. This embodiment differs from the first embodiment in that the fluid reservoir 12 is not pliable, but rather comprises a rigid enclosure. A flexible bladder 25 communicates with the interior of the fluid reservoir 12. The flexible bladder 25 serves to regulate the pressure in the fluid reservoir 12.

Figure 4:
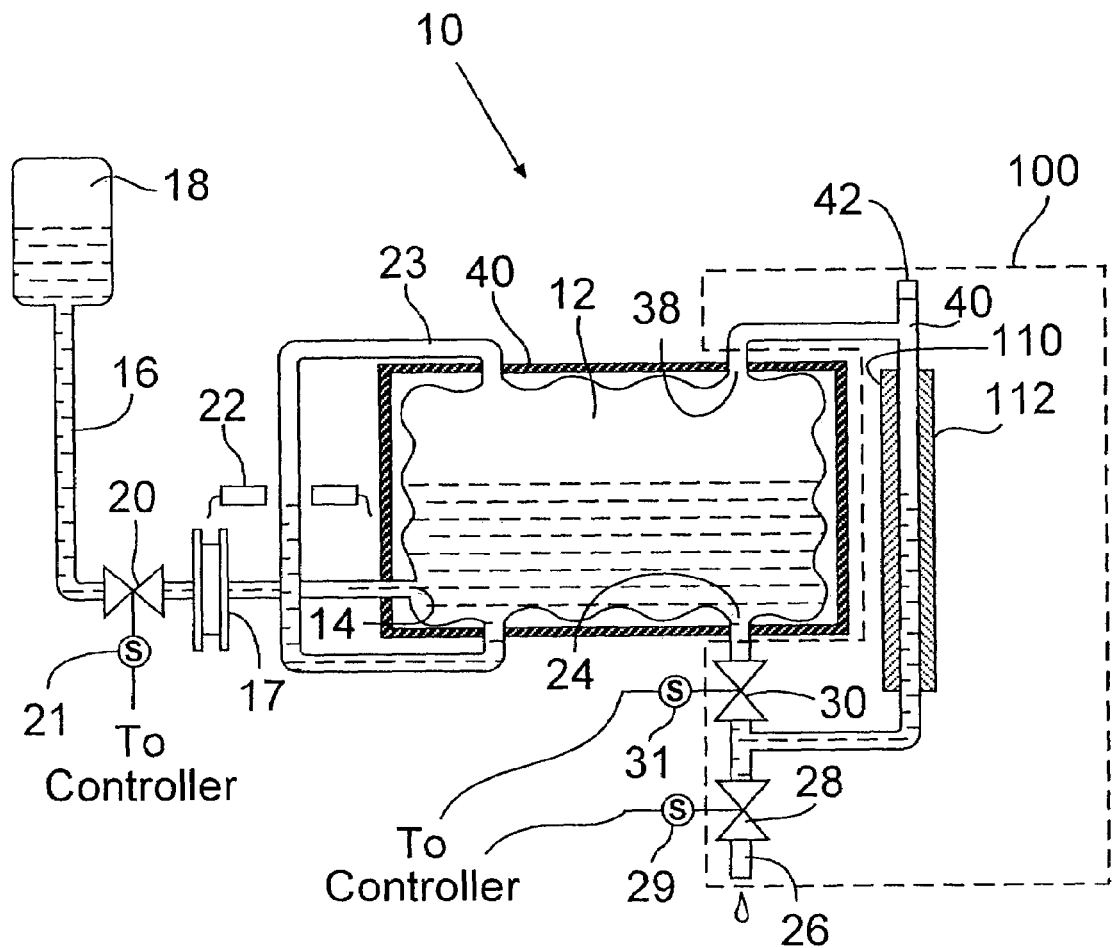
FIG. 4 is a schematic diagram illustrating another embodiment of the fluid dispensing apparatus 10 according to the present invention.
Figure 5:
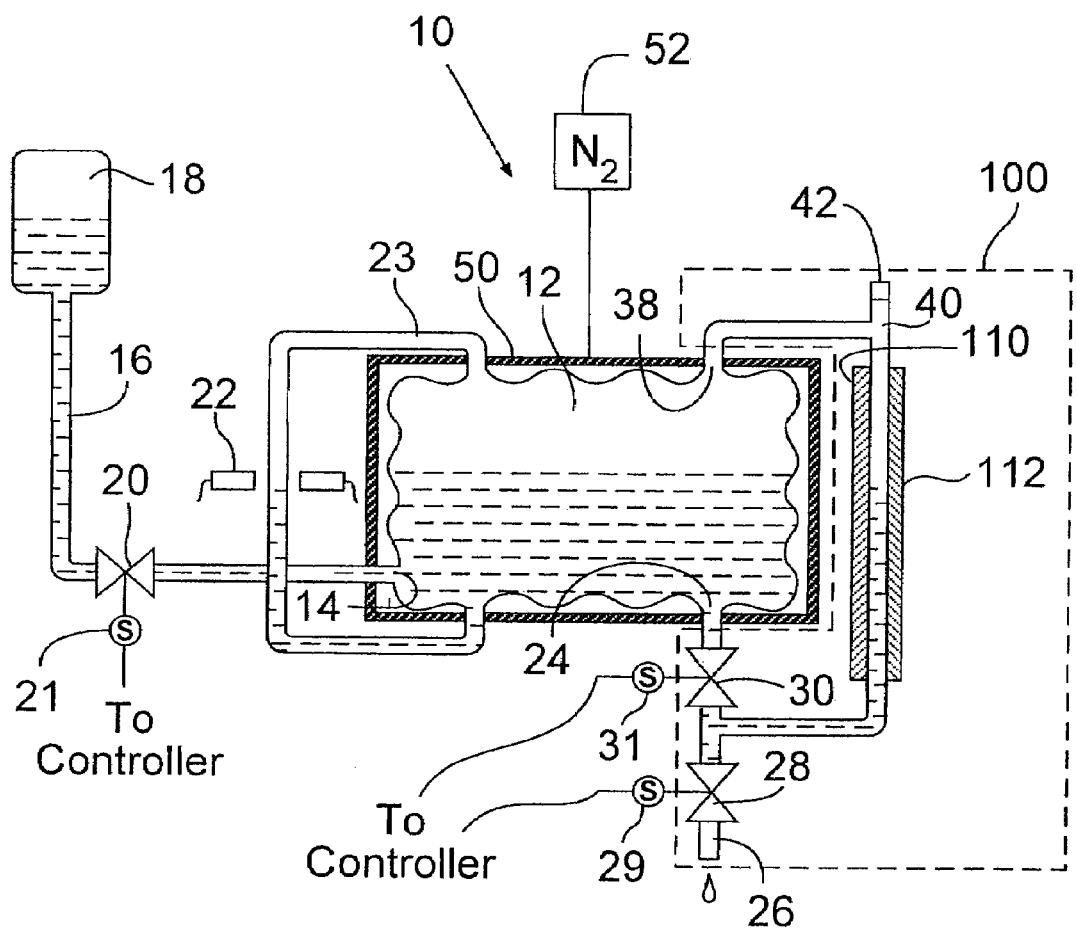
FIG. 5 is a schematic diagram illustrating another embodiment of the fluid dispensing apparatus 10 according to the present invention.

FIG. 4 illustrates another embodiment of the present invention. The embodiment shown in FIG. 4 is configured as a volumetric filler and is similar to the embodiment shown in FIG. 1. However, the embodiment shown in FIG. 4 includes a housing 40 which encloses a pliable fluid reservoir 12. The housing 40 can be, for example, constructed in two halves extending lengthwise to allow easy insertion and removal of the fluid reservoir 12 from the housing 40.

The housing 40 may serve simply as a containment vessel for the pliable fluid reservoir 12, or may itself be pressurized. If the housing 40 is used as a containment vessel, as shown in FIG. 4, a small opening can be placed in the housing 40 to allow pressure within the housing 40 to equalize with the pressure outside the housing, and thereby accommodating for accurate expansion and contraction of the fluid reservoir 12. Alternatively, the housing 40 can be constructed of a porous material.

For certain applications and/or fluids, the pressure exerted on the pliable fluid reservoir will not be the same as the pressure exerted elsewhere on the apparatus. If the housing 40 is pressurized or de-pressurized, air tight seals should be used between the housing 40 and the fluid reservoir at fill port 14, around the side tube 23, at vent 38, and at drain port 24.

Pressurization can be accomplished by, for example, by connecting a source 52 of pressurized gas (e.g., nitrogen) to the fluid dispensing apparatus such gas can be introduced into the space between housing 50 and pliable fluid reservoir 12. Both the housing 40 and reservoir 12 can be pressurized at the same time. If the housing 40 or the fluid reservoir 12 is pressurized, the clarification filter 17 should preferably be removed to avoid errors resulting from the pressure drop across the filter.

The present invention can be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

The invention claimed is:

1. A fluid dispensing apparatus for dispensing a predetermined volume of fluid comprising:
   (a) a fluid reservoir with a fluid inlet for the introduction of the fluid into said fluid reservoir, and a fluid outlet for the release of said fluid from said fluid reservoir;
   (b) a fill tube assembly connected to said fluid outlet, the fill tube assembly comprising
      (i) a fill valve capable of controlling the flow of fluid released from said fluid reservoir into the fill tube assembly, and
      (ii) a drain line provided with a discharge valve for dispensing a predetermined volume of fluid from said fill tube assembly; and
   wherein the fill tube assembly further consists of a means for continuously and electronically measuring fluid volume therein, said means consisting of a pair of electroconductive terminals proximate either said fill tube assembly or said fluid reservoir and means for connecting said terminals to an energy source so that a current can be passed from one terminal to the other terminal; and
   control means responsive to the capacitance of said current for selectively controlling said dispensing of fluid from said tube assembly, or said introduction of fluid from said reservoir, or said release of fluid from said reservoir.

2. The fluid dispensing apparatus of claim 1, wherein said electroconductive terminals consists essentially of electroconductive strips affixed to the external surface of said fill tube assembly.

3. The fluid dispensing apparatus of claim 2, wherein the electroconductive strips are both made substantially of copper.

4. The fluid dispensing apparatus of claim 1, wherein the current passed from one terminal to the other terminal is a pulsed current.

5. The fluid dispensing apparatus of claim 1, wherein the control means is operative to open manually the discharge valve for a determinable time period to thereby dispense a determinable volume of fluid.

6. The fluid dispensing apparatus of claim 1, wherein the fluid reservoir is pliable.

7. The fluid dispensing apparatus of claim 1, wherein the fluid reservoir is not pliable.

8. The fluid dispensing apparatus of claim 7 further comprising a bladder.

9. The fluid dispensing apparatus of claim 1, wherein the fluid reservoir is enclosed in a rigid housing.

10. The fluid dispensing apparatus of claim 1 further comprising a source of pressurized gas.

* * * * *